(12) United States Patent
Sandkuehler et al.

(10) Patent No.: US 10,324,013 B2
(45) Date of Patent: Jun. 18, 2019

(54) METHODS FOR SELECTING FILM STRUCTURES FOR PACKAGES

(71) Applicant: Dow Global Technologies LLC, Midland, MI (US)

(72) Inventors: Peter Sandkuehler, Horgen (CH); Prashant Sharad Shembekar, Mumbai Vikhroli (IN)

(73) Assignee: Dow Global Technologies LLC, Midland ( * ) Notice: Subject to any disclaimer, the term of this patent is extended or adjusted under 35 U.S.C. 154(b) by 0 days.

(21) Appl. No.: 15/558,235

(22) PCT Filed: Apr. 7, 2016

(86) PCT No.: PCT/US2016/026317
§ 371 (c)(1),
(2) Date: Sep. 14, 2017

(87) PCT Pub. No.: WO2016/176014
PCT Pub. Date: Nov. 3, 2016

(65) Prior Publication Data
US 2018/0045631 A1     Feb. 15, 2018

(30) Foreign Application Priority Data

Apr. 27, 2015   (IN) ........................... 2137/CHE/2015

(51) Int. Cl.
*G01M 7/00*       (2006.01)
*G01N 3/30*       (2006.01)
(Continued)

(52) U.S. Cl.
CPC ................ *G01N 3/30* (2013.01); *B32B 7/12* (2013.01); *B32B 27/08* (2013.01); *B32B 27/285* (2013.01);
(Continued)

(58) Field of Classification Search
CPC .... G01N 3/30; G01N 2203/0216; B32B 7/12; B32B 27/285; B32B 27/32; B32B 27/36;
(Continued)

(56) References Cited

U.S. PATENT DOCUMENTS

| 7,780,354 B2 | 8/2010 | Funaki et al. |
| 8,124,243 B2 | 2/2012 | Wright et al. |

(Continued)

FOREIGN PATENT DOCUMENTS

| GB | 1206373 A | 9/1970 |
| WO | 2013159836 A1 | 10/2013 |

OTHER PUBLICATIONS

PCT/US2016/026317, International Search Report & Written Opinion dated Jul. 6, 2016.
(Continued)

*Primary Examiner* — Max H Noori (57) ABSTRACT

Methods are provided that facilitate the selection of a film structure for use in a package. In one aspect, a method of selecting a film structure for use in a package comprises determining a critical impact direction of a package by finite elemental method (FEM) analysis, wherein the package has a predetermined volume, a predetermined shape, and a predetermined fill material; determining one or more desired tensile properties of a film structure to use in the package based on the critical impact direction, wherein the one or more desired tensile properties comprise at least one of toughness in the machine direction, toughness in the cross direction, elongation at break in the machine direction, elongation at break in the cross direction, stress at break in the machine direction, and stress at break in the cross direction; and selecting a film structure based on the one or more desired tensile properties.

20 Claims, 4 Drawing Sheets

(51) Int. Cl.
*G01M 7/08* (2006.01)
*G06F 17/50* (2006.01)
*B32B 7/12* (2006.01)
*B32B 27/32* (2006.01)
*B32B 27/36* (2006.01)
*B32B 27/28* (2006.01)
*B32B 27/08* (2006.01)
*B32B 27/34* (2006.01)

(52) U.S. Cl.
CPC .............. *B32B 27/32* (2013.01); *B32B 27/34* (2013.01); *B32B 27/36* (2013.01); *G01M 7/08* (2013.01); *G06F 17/5018* (2013.01); *B32B 2270/00* (2013.01); *B32B 2307/514* (2013.01); *B32B 2307/518* (2013.01); *B32B 2307/54* (2013.01); *B32B 2307/558* (2013.01); *B32B 2307/732* (2013.01); *B32B 2439/46* (2013.01); *B32B 2553/00* (2013.01); *G01N 2203/0216* (2013.01)

(58) Field of Classification Search
CPC .......... B32B 2270/00; B32B 2307/514; B32B 2307/518; B32B 2307/54; B32B 2307/558; B32B 2307/732; B32B 2553/00; G01M 7/08; G06F 17/5018
USPC ........................................ 73/962, 12.06, 826
See application file for complete search history.

(56) References Cited

U.S. PATENT DOCUMENTS

| | | | |
|---|---|---|---|
| 2003/0035598 A1* | 2/2003 | Hiraiwa | B65D 31/04 383/205 |
| 2006/0210743 A1 | 9/2006 | Bekele | |
| 2006/0243057 A1* | 11/2006 | Bailey | G01N 3/24 73/788 |
| 2009/0004415 A1 | 1/2009 | Niedersuess et al. | |
| 2009/0249858 A1* | 10/2009 | Ishikawa | G01D 3/10 73/12.06 |
| 2010/0148363 A1* | 6/2010 | Goh | H01L 21/561 257/738 |
| 2013/0074454 A1 | 3/2013 | Babrowicz | |
| 2015/0049964 A1* | 2/2015 | Bellmore | B32B 27/08 383/109 |
| 2016/0259865 A1* | 9/2016 | Neerukonda | B65B 35/00 |
| 2017/0286579 A1* | 10/2017 | Shen | G06F 17/5018 |

OTHER PUBLICATIONS

PCT/US2016/026317, International Preliminary Report on Patentability dated Oct. 31, 2017.
Gonzalez E.V. et al: "Simulation of drop-weight impact and compression after impact tests on composite laminates", Composite Structures, vol. 94, No. 11, pp. 3364-3378, XP028502072.
Lonn et al., Drop Test of a soft beverage package-experimental tests and a parameter study in abaqus, pp. 1-80, 2006.
Mameli et al., "Stimulating the Pouch Forming Process Using a Detailed Fluid-Structure Interaction", 2013 SIMULIA Customer Conference, pp. 1-15.
Menrad et al., "Drop Test of Plastic Packagings—Correlation with Material Parameters and Change of Packaging Bahaviour After Impact of Standard Liquids", Packaging Technology and Science, 2013.
P.E. Reed et al: "Simulation of the drop impact test for moulded themoplactics containers", International Journal of Impact Engineering., vol. 24, No. 2, Feb. 1, 2000 (Feb. 1, 2000), pp. 133-153, XP055282899.
Tekamp, D., "Computational Methods of Analyzing Stretch Film Performance", AMI Stretch & Shrink Film Conference, New Orleans, LA, Nov. 11-12, 2014, pp. 1-30.
Watanable et al, Variation in Pressure in Liquid-Filled Plastic Film Bags Subjected to Drop Impact, Materials Transaction, vol. 53, No. 2, pp. 291-295, 2012.
Yuan C. et al: "Dynamic response of flexible container during the impact with the ground", International Journal of Impact Engineering, Pergamon, GB, vol. 37, No. 10, Oct. 1, 2010 (Oct. 1, 2010), pp. 999-1007, XP027122813.
Yuan, J. et al., "Predictive Analysis of Flexible Pouch Performance", SPE ANTEC 2014, pp. 1436-1440.

* cited by examiner

METHODS FOR SELECTING FILM STRUCTURES FOR PACKAGES

FIELD

The present invention relates to methods for selecting film structures for packages.

INTRODUCTION

Drop tests of packaging pouches and bags are frequently carried out to ensure that pouches will not break and open if accidentally dropped during transportation and usage. Typically, for a given packaging application (e.g., detergent liquid, pet food, etc.), the critical drop height is specified by the transportation requirements. Various tests are carried out with different packaging materials until a packaging structure meets the drop test requirements. Such tests can be time intensive as the package has to be constructed and tested before evaluating the results and, if necessary, modifying the components and/or construction of the package.

It would be desirable to have an improved method for evaluating and selecting film structures for use in packages so as to shorten the time required to design a package that meets performance requirements.

SUMMARY

The present invention advantageously provides methods that facilitate selection of film structures to meet certain performance requirements and in particular, critical drop test requirements. For example, based on a particular pouch or bag format and desired drop test requirements, embodiments of the present invention can assist in the selection of film structures having mechanical properties in the machine and cross directions to provide pouches or bags meeting such requirements. Embodiments of such methods can allow improvements in drop height based on targeted engineering of the mechanical properties of the laminate or film which will survive specific drop heights in a given pouch format with a given pouch filling.

In one aspect, a method of selecting a film structure for use in a package comprises determining a critical impact direction of a package by finite elemental method (FEM) analysis, wherein the package has a predetermined volume, a predetermined shape, and a predetermined fill material; determining one or more desired tensile properties of a film structure to use in the package based on the critical impact direction, wherein the one or more desired tensile properties comprise at least one of toughness in the machine direction, toughness in the cross direction, elongation at break in the machine direction, elongation at break in the cross direction, stress at break in the machine direction, and stress at break in the cross direction; and selecting a film structure based on the one or more desired tensile properties.

In another aspect, a method of selecting a film structure for use in a package comprises conducting a drop test of a package at a specified height, wherein the package has a predetermined volume, a predetermined shape, and a predetermined fill material;

analyzing the impact stress on a plurality of regions of the package during the drop test; determining one or more desired tensile properties of a film structure to use in the package based on analysis of the impact stress, wherein the one or more desired tensile properties comprise at least one of toughness in the machine direction, toughness in the cross direction, elongation at break in the machine direction, elongation at break in the cross direction, stress at break in the machine direction, and stress at break in the cross direction; and selecting a film structure based on the one or more desired tensile properties.

These and other embodiments are described in more detail in the Detailed Description.

DETAILED DESCRIPTION

Embodiments of the present invention advantageously provide methods that facilitate the selection of film structures with appropriate mechanical properties to survive a required critical drop height after being formed into a packaging pouch or bag. In some embodiments, finite element method ("FEM") analysis is utilized to determine, for example, a critical impact direction of a pouch. The results of the FEM analysis can advantageously facilitate the selection of a film structure with certain mechanical properties to impart the desired performance requirements (e.g., drop height) to a pouch or bag constructed from such film structure. In some embodiments, methods of the present invention facilitate the selection of optimal packaging to advantageously satisfy drop test requirements while minimizing material (e.g., film) usage. As used herein, the term "film structure" should be understood to include monolayer films, coextruded multilayer films, laminates, and other polymeric films typically used to form packages.

In one aspect, the present invention provides a method of selecting a film structure for use in a package that comprises determining a critical impact direction of a package by FEM analysis, wherein the package has a predetermined volume, a predetermined shape, and a predetermined fill material; determining one or more desired tensile properties of a film structure to use in the package based on the critical impact direction, wherein the one or more desired tensile properties comprise at least one of toughness in the machine direction, toughness in the cross direction, elongation at break in the machine direction, elongation at break in the cross direction, stress at break in the machine direction, and stress at break in the cross direction; and selecting a film structure based on the one or more desired tensile properties. In some embodiments, determining the critical impact direction of a package comprises conducting a drop test at a specified height.

In another aspect, the present invention provides a method of selecting a film structure for use in a package that comprises conducting a drop test of a package at a specified height, wherein the package has a predetermined volume, a predetermined shape, and a predetermined fill material; analyzing the impact stress on a plurality of regions of the package during the drop test; determining one or more desired tensile properties of a film structure to use in the package based on analysis of the impact stress, wherein the one or more desired tensile properties comprise at least one of toughness in the machine direction, toughness in the cross direction, elongation at break in the machine direction, elongation at break in the cross direction, stress at break in the machine direction, and stress at break in the cross direction; and selecting a film structure based on the one or more desired tensile properties.

In another aspect, a method of manufacturing a film structure for use in a package comprises conducting a drop test of a package at a specified height, wherein the package has a predetermined volume, a predetermined shape, and a predetermined fill material; analyzing the impact stress on a plurality of regions of the package during the drop test; determining one or more desired tensile properties of a film structure to use in the package based on analysis of the impact stress, wherein the one or more desired tensile properties comprise at least one of toughness in the machine direction, toughness in the cross direction, elongation at break in the machine direction, elongation at break in the cross direction, stress at break in the machine direction, and stress at break in the cross direction; selecting a film structure based on the one or more desired tensile properties; and manufacturing the film structure.

The drop test, in some embodiments, is performed according to ASTM D5276-98 and ASTM D2463-10b (procedure B).

In some embodiments, the package to be formed from the film structure is a pouch. The fill material to be used in the package can comprise, in various embodiments, a liquid or a plurality of solids.

The selection of the film structure can comprise, in some embodiments, determining the number of layers to use within the film structure, determining a thickness of the film structure, determining the composition of each layer within the film structure, and/or determining manufacturing conditions for forming the film structure. In general, methods of the present invention can be used in the manufacture of a wide variety of film structures formed from a wide variety of compositions. For example, in some embodiments, the film structure can comprise a coextruded film structure comprising at least one film layer having greater than 50% polyethylene by weight. The film structure, in some embodiments, can comprise an adhesively laminated, coextruded film structure comprising at least one film layer having greater than 50% polyethylene by weight. In some embodiments, selecting a film structure further comprises minimizing the thickness of the film structure while providing the one or more desired tensile properties.

In general, embodiments of the present invention are directed to methods of selecting film structures for use in packages and to methods of manufacturing film structures for use in packages. Embodiments of the present invention can be implemented with a wide variety of packages known to those of skill in the art including, for example, bags, pouches (including stand-up pouches), four corner pouches, pre-made pouches and bags, gusseted pouches, containers, lidded soft trays, lidded hard trays, and pouches and packages with additional features such as, for example, reclose zippers, reclose with hook and fastener systems (e.g., Velcro), spouts, and pouches made by a variety of sealing methods (e.g., heat sealing, laser sealing, and ultrasound sealing). Further, embodiments of the present invention can be implemented for packages intended to contain a wide variety of fill materials including, for example, one or more solids, one or more liquids, one or more gels, one or more gases (including, for example, fill air), and combinations thereof (e.g., solid materials encapsulating gels, solid materials encapsulating a gas, etc.), etc. In general, embodiments of the present invention can be used in the design of packages to hold, contain, and/or transport food products, cleaning supplies, dishwashing and laundry detergents, pet foods, beverages, and other items that will be apparent to those of skill in the art based on the teachings herein.

Packages and potential packages are often evaluated based on certain performance criteria depending on the intended usage and transportation requirements for the package. As noted above, drop tests of packaging pouches and bags are frequently carried out to ensure that the pouches and bags will not break and open if accidentally dropped during transportation and/or usage. For a given packaging application with drop test requirements, the critical drop height is often dictated by the transportation requirements. While this application may frequently discuss the design of film structures for packages having drop test requirements, it should be understood that the methodology can be applied in designing film structures for packages having other performance requirements. Other performance requirements can include mechanical resistance (without leakers and failures), vibrations during transportation (ASTM D 4916 -05), flexibility and fatigue failure as simulated in the GELBO flex crack test, and/or the self-standing ability of the packages on shelves.

Embodiments of the present invention utilize FEM analysis to determine a critical impact direction of a package. FEM analysis is a modeling technique well known to those in the field of mechanical engineering and other disciplines. One challenge with FEM simulations is the quality of the input material models. For example, it can be difficult to accurately characterize complex material combinations, such as, for example, an engineering strain at break of 25% for an oriented PET film in combination with a polyethylene film having an engineering strain at break of 700%. Film structures for packages are typically multi-material composites which often have different mechanical properties in each layer, in addition to some layers often being bonded adhesively. Embodiments of the present invention advantageously utilize realistic FEM simulations that capture the complexity of packaging film structures.

With commercial software packages for FEM simulations, there do not appear to be any ready to use material models for simulating highly non-linear orthotropic material behavior, particularly in connection with flexible packaging materials. Thus, in carrying out some embodiments of the present invention, a material model to simulate such behavior can be developed within the framework of existing commercial software for FEM analysis. For example, film materials for packaging applications, such as laminates, are not homogeneous at a micro level, and the individual layers flow and deform differently. Thus, such a material model needs to be able to capture this structural behavior and to make provisions for different flow characteristics that represent the actual stress-strain behavior along the two primary orthogonal directions—machine direction and cross direction.

Other challenges associated with FEM analysis of thin laminate structures include the numerical instability due to excessive rotation of an element in one increment under high speed impact, and the deeper penetration of fluid particles into the laminate structure due to inadequate contact constraints as a result of lower mass of the laminate. Again, in some embodiments, these challenges are accounted for in developing a material model to simulate behavior of the laminate structures.

A number of commercial software packages are available for use in conducting FEM analysis. Non-limiting examples of such software packages include Abaqus Unified FEA commercially available from Dassault Systems, LS-DYNA commercially available from Livermore Software Technology Corporation, and ANSYS CFX or ANSYS Fluent coupled with ANSYS Mechanical, which are commercially available from ANSYS, Inc.

The FEM analysis software can be used to simulate performance in accordance with some embodiments of the present invention. For example, FEM analysis software can be set up to simulate drop test performance of a package. In such embodiments, a package (e.g., a pouch) can be designed and its mechanical property analyzed in a simulated drop test from a critical drop height. A number of package parameters can be specified (and likewise varied) as part of the simulation to evaluate how a particular parameter impacts performance of the package. In the case of pouches formed from films, for example, package properties that can be varied/specified can include thickness of the film structure, the aspect ratio of the pouch, the form of the pouch, the volume of the pouch, the type of fill material in the pouch, the mechanical properties of the film and/or laminate, the structure of the film or laminate, and others.

Once the package (and fill material) properties are specified, in the case of drop impact testing, the FEM analysis can simulate the dropping of the package from a specified height and model various mechanical properties of the package and various heights during the drop. For example, in the simulation for drop impact testing, the FEM analysis can provide data regarding the stress-strain response of the film structure (in machine and cross directions for a given film structure), toughness in the machine direction, toughness in the cross-direction, elongation at break in the machine direction, elongation at break in the cross direction, stress at break in the machine direction, stress at break in the cross direction, and the maximum load (force, stress) that the laminate or film is exposed to in either machine or cross direction.

The results of the FEM analysis can advantageously permit one to determine a critical impact direction of a package undergoing a drop test. A package may drop on a surface on one of multiple surfaces of the package. For example, a typical stand up pouch (SUP) might fall and land on its bottom, on its top, on it flat front or flat rear surface, or on its side. Typically, one of these sides is the most critical for material failure to occur, and will have the lowest critical drop height it can withstand before breaking. This is referred to as the critical impact direction, and persons of skill in the art will understand that other types of packages will similarly have a critical impact direction. For example, the FEM analysis may advantageously show the area(s) of a package that are under the greatest stress when the package hits a surface in a drop test (i.e., the impact stress). The portion of the package under heightened impact stress can vary from package-to-package depending on a number of factors including, for example, the dimensions of the package, the volume of the package, the fill material, the amount of fill material in the package, the film structure used to form the package, and others. This area can be identified by reviewing information generated by the FEM analysis including, without limitation, a visual representation of the stresses on the simulated bag, raw data generated by the FEM analysis of maximum stresses in predefined directions, etc.

After determining a critical impact direction (such as an impact stress in the case of a drop or similar test), one can select a film structure for use in the package. For example, one can consider the information from the FEM analysis in determining the number of layers for the film structure, the thickness of the film, the composition of each layer in the film structure (e.g., type of polymer, properties of the polymer, whether to include multiple polymers, etc.), whether to include multiple films via adhesive lamination, whether to include duplex (two adhesively bonded films)/triplex/quadruplex structures, the choice of adhesive (if any), and manufacturing conditions for forming the film structure (e.g., blown vs. cast film; whether to orient the film in the machine, cross, or both directions; type of seal). In some instances, when one has flexibility in selecting the dimensions or shape of a package (or other package parameters), one may choose to modify the dimensions of the package and conduct the FEM analysis again to see if the modifications change the impact stress of the package. In some embodiments, the film structure can be selected so as to minimize the thickness of the film structure (or the amount of polymer used to make the film) while providing the one or more desired tensile properties.

Once a film structure is selected, in some embodiments, a package sample can be constructed and tested. While modifications to the film structure may be required based on testing of an actual package, one benefit of some embodiments of the present invention is to reduce the amount of time required to select a film structure by reducing the number of package prototypes that need to be constructed, tested, and/or modified in order to achieve the desired performance Some embodiments of the invention will now be described in detail in the following Examples.

EXAMPLES

Example 1

Figure 1:
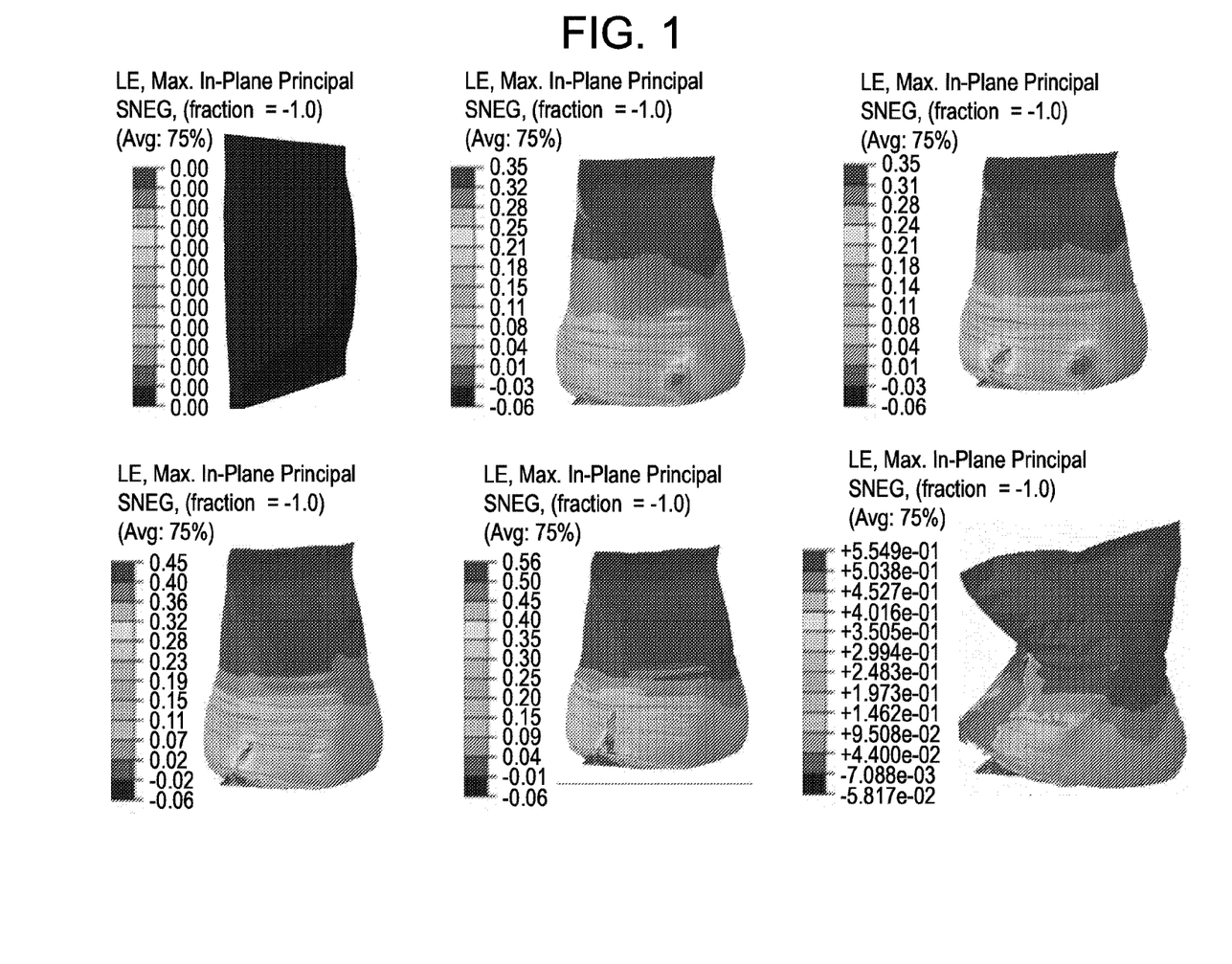
FIG. 1 is a series of simulated images of a pouch at different stages of a vertical drop impact.

In this example, FEM analysis is used to simulate how a pouch without seal seams, and filled with water, deforms and fails upon impact. FIG. 1 shows a series of simulated images of the pouch at different stages of a vertical drop impact. The colors from blue to red in the images indicate increasing strain in the laminate.

The important features shown in the simulated vertical drop impact are the elongation of the laminate in the central lower part of the pouch which is associated with an increasing stress concentration in that area, and which leads to eventual failure of the laminate by rupturing. This represents a critical impact direction of this pouch.

Figure 2:
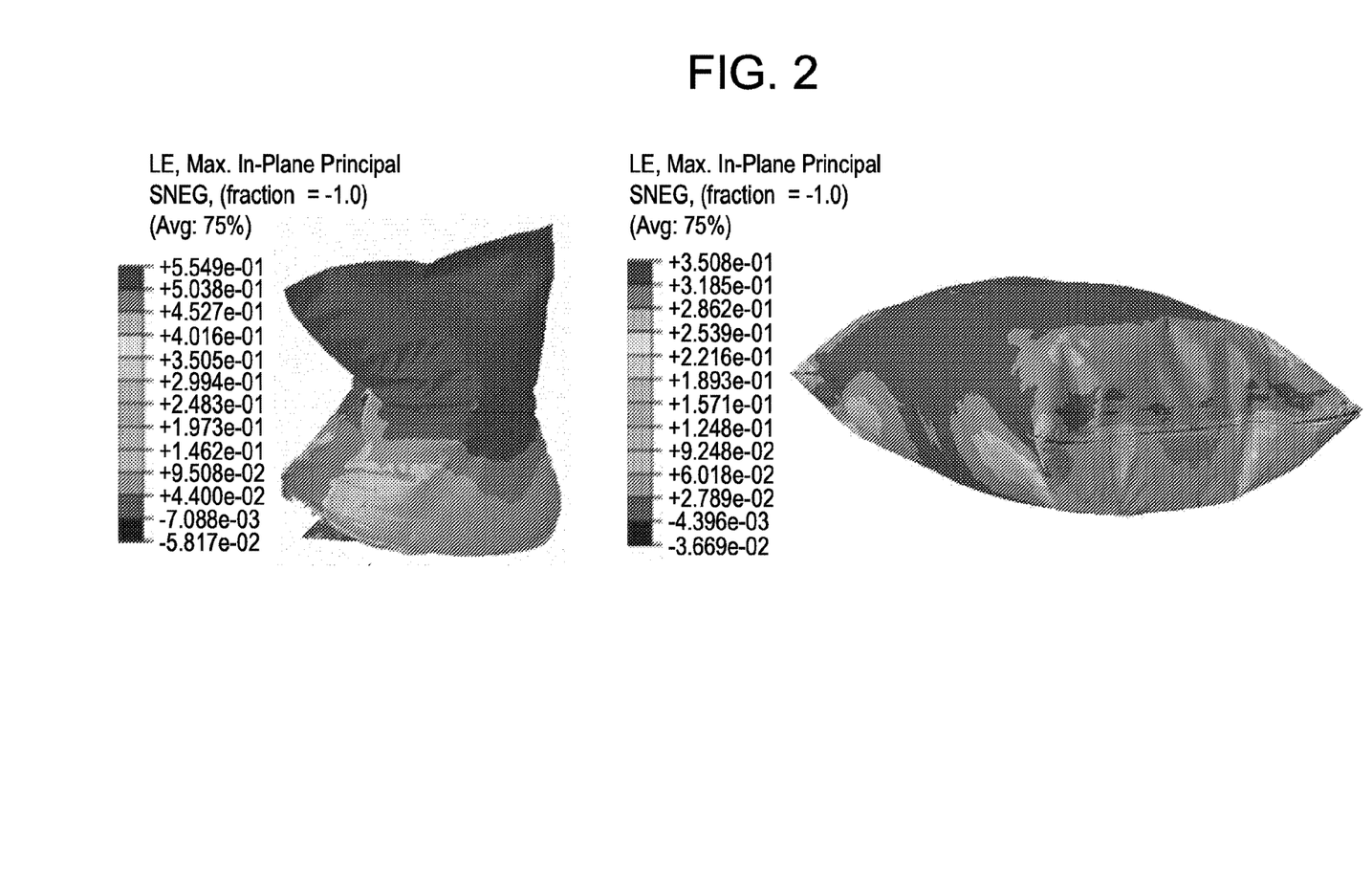
FIG. 2 provides simulated images of a pouch impacting a surface vertically on the left and horizontally on the right.

The critical impact direction chosen in the FEM analysis simulation can play an important role as well for a given filling volume. For example, whereas pouches dropped vertically are predicted to break, pouches impacting on the flat, larger side are not expected to burst. This comparison is illustrated in the FEM analysis simulation in FIG. 2 with the pouch impacting vertically on the left and horizontally on the right. The pouch is idealized and without seal seams in this simulation. The pouch that impacts vertically breaks, whereas the pouch that impacts horizontally on the larger side does not.

Optimized Example 1 and Comparative Example 1

As shown in the FEM analysis in Example 1, vertical drops onto the bottom seal are the most critical in terms of drop height performance for the pillow pouches that were chosen as the sample pack for the example. Considering the pouch deformation observed in the FEM simulation of a drop in FIG. 1, which to a significant degree occurred in cross/transverse direction (CD) of the laminate formed into a pouch or bag on a vertical form fill seal machine, a set of experiments is carried out using laminates with different CD and machine direction (MD) tensile properties.

Two laminates are selected for drop testing. The detailed film structures and compositions of the two laminates are provided in Table 1. The biaxially-oriented polypropylene and biaxially-oriented PET layers are standard materials that are commercially available from a variety of sources. ADCOTE™ 675A and 675C are solvent-based polyurethane adhesive systems commercially available from The Dow Chemical Company. DOWLEX™ NG 5056G is a LLDPE resin with a density of 0.919 g/cm$^3$ and a melt index ($I_2$) of 1 g/10 minutes, which is commercially available from The Dow Chemical Company. ELITE™ 5401GS is an enhanced polyethylene resin with a density of 0.916 g/cm$^3$ and a melt index ($I_2$) of 1 g/10 minutes, which is commercially available from The Dow Chemical Company. DOW™ LDPE 310E is a LDPE resin with a density of 0.9235 g/cm$^3$ and a melt index ($I_2$) of 0.75 g/10 minutes, which is commercially available from The Dow Chemical Company.

TABLE 1

Laminate and Film structure of the Sample Laminates

| LAMINATE | SUB | ADHESIVE | LAYER A (10 μm) | LAYER B (30 μm) | LAYER C (10 μm) |
|---|---|---|---|---|---|
| Comparative Example 1 (Comp. Example 1) | BOPP (20 μm) | Adcote 675A + 675C | Dowlex NG5056G + 20% LDPE 310E | Dowlex NG5056G + 20% LDPE 310E | Elite 5401GS |
| Optimized Example 1 (Opt. Example 1) | OPET (12 μm) | Adcote 675A + 675C | Dowlex NG5056G + 20% LDPE 310E | Dowlex NG5056G + 20% LDPE 310E | Elite 5401GS + 50% LDPE 312E |

Figure 3:
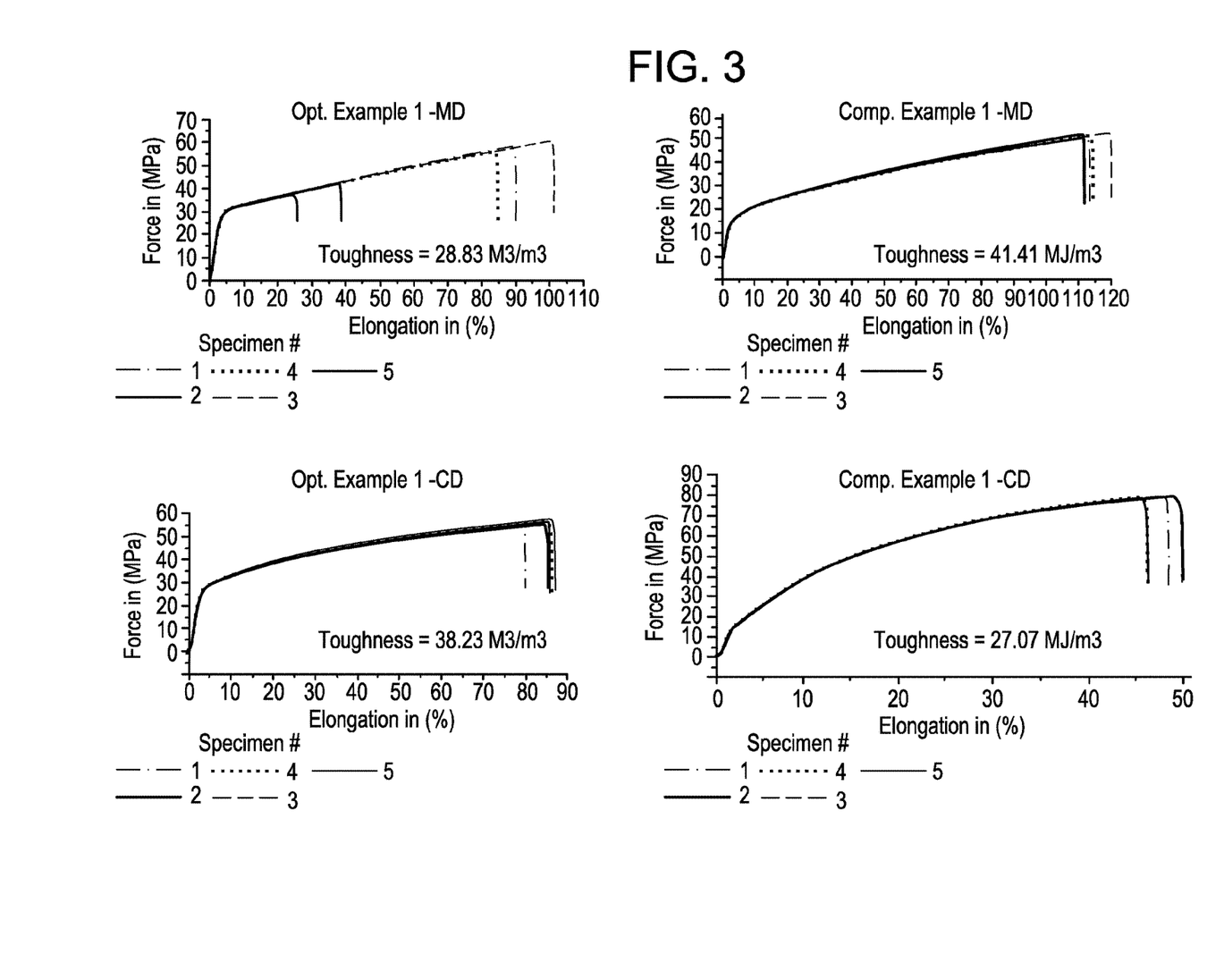
FIG. 3 includes tensile curves showing tensile toughness for the laminates prepared in connection with Optimized Example 1 and Comparative Example 1.

The two laminates are characterized in tensile testing with the results reported in Table 2. These two different laminates are chosen for the drop testing as they have opposite tensile strength and elongation at break behavior in the machine direction (MD) and cross direction (CD). FIG. 3 provides the full tensile curves of the two chosen laminates.

TABLE 2

Tensile Characterization of Laminates

| Sample | | | Thickness* (μm) | Tensile stress at Break (MPa) | Tensile strain at Break (%) | Toughness (MJ/m$^3$) |
|---|---|---|---|---|---|---|
| Comp. Example 1 | CD | Mean | 75.00 | 77.20 | 46.96 | 27.07 |
| | | SD | 0.00 | 3.03 | 2.03 | 1.30 |
| | MD | Mean | 75.00 | 51.19 | 113.71 | 41.41 |
| | | SD | 0.00 | 0.90 | 3.46 | 1.72 |
| Opt. Example 1 | CD | Mean | 63.00 | 56.59 | 84.26 | 38.23 |
| | | SD | 0.00 | 0.78 | 2.68 | 1.52 |
| | MD | Mean | 63.00 | 49.36 | 67.54 | 28.83 |
| | | SD | 0.00 | 10.60 | 33.46 | 16.90 |

The laminates are formed into pillow pouches on the Bosch VFFS line. The pouch height is set on the machine to 300mm, and width is kept constant at 155 mm The sealing conditions used both on the Bosch VFFS line and later for forming manual seals (for top and bottom seals) are 150° C., 0.3 s and 5.4 bars for laminate Comparative Example 1 and 140° C., 0.2 s and 5.4 bar for Optimized Example 1. Different sealing conditions are chosen in order to obtain equivalent seal strength when comparing the machine seal with the manual seals on the lab sealer, and to maximize seal performance for each laminate (strength and hermeticity). The sealing temperature used for the lateral seal is kept constant at 185° C. on the VFFS. The original pouches are cut open, removing the top seal, filled with the specified amount water and resealed, resulting in a new height of 273.7 mm with a standard deviation of 1.8 mm Volumes of 0.7, 0.9 and 1.05 L of water are filled in the pouch and drop tested.

Figure 4:
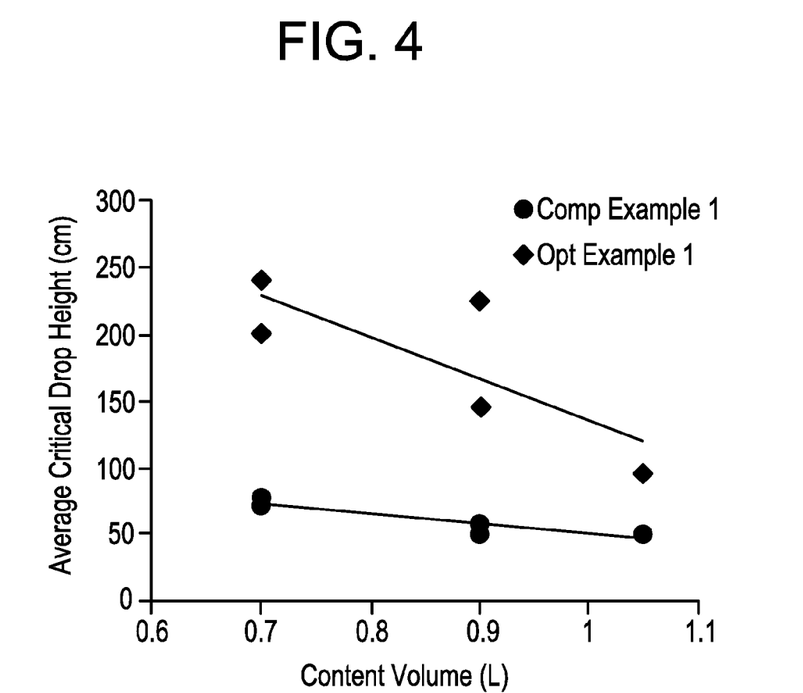
FIG. 4 is a chart of average critical drop height versus filling volume for the laminates prepared in connection with Optimized Example 1 and Comparative Example 1.

Drop tests were performed in accordance with ASTM D5276-98 and ASTM D2463-10b (procedure B) using the staircase method. ASTM D5276-98 describes how to drop test pouches and ASTM D2463-10b (procedure B) provides statistical tools that return an average critical drop height and its corresponding standard deviation. FIG. 4 shows the critical drop height as a function of filling volume for Optimized Example 1 and Comparative Example 1, with linear regression trend lines added.

The two different laminates formed into pouches show a different critical drop height. The laminate providing the higher critical drop height in the drop test (Optimized Example 1) is the one with the higher toughness and elongation at break in the CD direction of the laminate. While further experiments may be needed to validate these initial tests, it appears that the FEM analysis from Example 1 (which showed the importance of CD strain at break, or toughness) led to the selection of a laminate which indeed achieved a higher critical drop height.

Optimized Examples 2 and 3 and Comparative Example 2 and 3

Optimized Examples 2 and 3 and Comparative Examples 2 and 3 are prepared in accordance with Table 3. The laminates include 3-layer coextruded polyethylene films that are made on a blown film line with a 200 mm die.

TABLE 3

Optimized Examples 2 and 3 and Comparative Examples 2 and 3

| LAMINATE | SUBSTRATE | ADHESIVE | LAYER A | LAYER B | LAYER C |
|---|---|---|---|---|---|
| Optimized Example 2 | OPA (13.5 μm) | MORFREE™ 698 + C79 | DOWLEX™ NG 5056G (10 μm) | AFFINITY™ PF 1140G (10 μm) | DOWLEX™ NG 5056G (10 μm) |
| Comparative Example 2 | OPA (13.5 μm) | MORFREE™ 698 + C79 | ELITE™ 5960G (10 μm) | ELITE™ 5960G (10 μm) | ELITE™ 5960G (10 μm) |
| Optimized Example 3 | OPET (12 μm) | MORFREE™ 698 + C79 | ATTANE™ SL 4100G (12.5 μm) | DOWLEX™ NG 5056G + 20% DOW™ LDPE 310E (12.5 μm) | ATTANE™ SL 4100G (12.5 μm) |
| Comparative Example 3 | OPET (12 μm) | MORFREE™ 698 + C79 | AFFINITY™ PF 1140G (10 μm) | DOWLEX™ NG 5056G (10 μm) | AFFINITY™ PF 1140G (10 μm) |

The biaxially-oriented polyamide and biaxially-oriented PET layers are standard materials that are commercially available from a variety of sources. MORFREE™ 698 and C79 are solvent-less polyurethane adhesive systems commercially available from The Dow Chemical Company. DOWLEX™ NG 5056G is a LLDPE resin with a density of 0.919 g/cm$^3$ and a melt index ($I_2$) of 1 g/10 minutes, which is commercially available from The Dow Chemical Company. AFFINITY™ PF 1140G is a plastomer polyethylene copolymer resin with a density of 0.896 g/cm$^3$ and a melt index ($I_2$) of 1.6 g/10 minutes, which is commercially available from The Dow Chemical Company. ELITE™ 5960G is an enhanced polyethylene resin with a density of 0.960 g/cm$^3$ and a melt index ($I_2$) of 0.85 g/10 minutes, which is commercially available from The Dow Chemical Company. ATTANE™ SL 4100G is an ultra low density polyethylene resin with a density of 0.912 g/cm$^3$ and a melt index ($I_2$) of 1 g/10 minutes, which is commercially available from The Dow Chemical Company. DOW™ LDPE 310E is a LDPE resin with a density of 0.9235 g/cm$^3$ and a melt index ($I_2$) of 0.75 g/10 minutes, which is commercially available from The Dow Chemical Company.

Tensile properties are measured on the substrate films and the results are shown in Table 4. Table 5 shows the tensile properties of the 3-layer coextruded polyethylene films.

TABLE 4

Tensile Properties of Substrate Films, OPET (12 μm) and OPA (13.5 μm)

|  | OPET (12 μm) | OPA (13.5 μm) |
|---|---|---|
| Stress at break MD (MPa) | 138.0 | 159.9 |
| Strain at break MD (%) | 25.7 | 22.8 |
| Toughness MD (MJ/m$^3$) | 26.1 | 21.2 |
| Stress at break CD (MPa) | 149.3 | 103.07 |
| Strain at break CD (%) | 26.3 | 23.2 |
| Toughness CD (MJ/m$^3$) | 31.6 | 20.6 |

TABLE 5

Tensile Properties of 3-layer Coextruded Polyethylene Films used in Examples in Table 3.

|  | Optimized Example 2 | Comp. Example 2 | Optimized Example 3 | Comp. Example 3 |
|---|---|---|---|---|
| Stress at break MD (MPa) | 30.36 | 28.0 | 27.8 | 29.4 |
| Strain at break MD (%) | 463.4 | 390.8 | 492.7 | 407.6 |
| Toughness MD (MJ/m$^3$) | 58.9 | 94.03 | 67.3 | 55.1 |
| Stress at break CD (MPa) | 28.6 | 16.5 | 27.5 | 23.8 |
| Strain at break CD (%) | 639.3 | 98.3 | 641.4 | 656.4 |
| Toughness CD (MJ/m$^3$) | 69.2 | 15.8 | 67.8 | 60.4 |

The coextruded polyethylene films are adhesively laminated on a 400 mm wide pilot line laminator to the substrate films as indicated in Table 3. The laminates are cured and formed into pillow pouches on a continuous vertical form fill seal line. The pouches are filled with 1.2 L of water and have dimensions of 270 mm in height and 150 mm width. Drop tests were performed in accordance with ASTM D5276-98 and ASTM D2463-10b (procedure B) using the staircase method. The data of critical drop height versus filling volume for vertical drops are summarized in Table 6.

TABLE 6

Critical drop height for Optimized Examples 2 and 3 and Comparative Examples 2 and 3 in Table 3

|  | Critical drop height (cm) |
|---|---|
| Optimized Example 2 | 290 |
| Comparative Example 2 | 50 |
| Optimized Example 3 | 116 |
| Comparative Example 3 | 42 |

Optimized Example 2 and Comparative Example 2 include the same OPA substrate film. Based on the simulations from Example 1 for pillow pouches, the CD tensile properties of Optimized Example 2 were optimized to provide a significantly higher critical drop height as compared to Comparative Example 2.

Likewise, Optimized Example 3 and Comparative Example 3 contain the same OPET substrate film. Based on the simulations from Example 1 for pillow pouches, the CD tensile properties of Optimized Example 3 were optimized to provide a higher critical drop height as compared to Comparative Example 3.

That which is claimed is:

1. A method of selecting a polymeric film structure for use in a package, comprising:
   determining a critical impact direction of a package by FEM analysis, wherein the package has a predetermined volume, a predetermined shape, and a predetermined fill material;
   determining one or more desired tensile properties of a polymeric film structure to use in the package based on the critical impact direction, wherein the one or more desired tensile properties comprise at least one of toughness in the machine direction, toughness in the cross direction, elongation at break in the machine direction, elongation at break in the cross direction, stress at break in the machine direction, and stress at break in the cross direction; and
   selecting a polymeric film structure based on the one or more desired tensile properties.

2. The method of claim 1, wherein determining the critical impact direction of a package comprises conducting a drop test at a specified height.

3. A method of selecting a polymeric film structure for use in a package, comprising:
   conducting a drop test of a package at a specified height, wherein the package has a predetermined volume, a predetermined shape, and a predetermined fill material;
   analyzing the impact stress on a plurality of regions of the package during the drop test;
   determining one or more desired tensile properties of a polymeric film structure to use in the package based on analysis of the impact stress, wherein the one or more desired tensile properties comprise at least one of toughness in the machine direction, toughness in the cross direction, elongation at break in the machine direction, elongation at break in the cross direction, stress at break in the machine direction, and stress at break in the cross direction; and
   selecting a polymeric film structure based on the one or more desired tensile properties.

4. The method of claim 3, wherein the impact stress on the package is analyzed using a computer database comprising FEM data.

5. The method of claim 2, wherein the drop test is ASTM D5276-98 or ASTM D2463-10b (Procedure B).

6. The method of claim 1, wherein selecting the film structure comprises at least one of determining a number of layers within the film structure, determining a thickness of the film structure, determining the composition of each layer within the film structure, and determining manufacturing conditions for forming the film structure.

7. The method of claim 1, wherein the film structure comprises a coextruded film structure comprising at least one film layer having greater than 50% polyethylene by weight.

8. The method of claim 1, wherein the film structure comprises an adhesively laminated coextruded film structure comprising at least one film layer having greater than 50% polyethylene by weight.

9. The method of claim 1, wherein the package is a pouch.

10. The method of claim 1, wherein the fill material is a liquid.

11. The method of claim 1, wherein the fill material comprises a plurality of solids.

12. The method of claim 1, wherein selecting a film structure further comprises minimizing the thickness of the film structure while providing the one or more desired tensile properties.

13. A method of manufacturing a polymeric film structure for use in a package, comprising:
   conducting a drop test of a package at a specified height, wherein the package has a predetermined volume, a predetermined shape, and a predetermined fill material;
   analyzing the impact stress on a plurality of regions of the package during the drop test;
   determining one or more desired tensile properties of a polymeric film structure to use in the package based on analysis of the impact stress, wherein the one or more desired tensile properties comprise at least one of toughness in the machine direction, toughness in the cross direction, elongation at break in the machine direction, elongation at break in the cross direction, stress at break in the machine direction, and stress at break in the cross direction;
   selecting a polymeric film structure based on the one or more desired tensile properties; and
   manufacturing the polymeric film structure.

14. The method of claim 13, wherein the impact stress on the package is analyzed using a computer database comprising FEM data.

15. The method of claim 14, wherein the drop test is ASTM D5276-98 or ASTM D2463-10b (Procedure B).

16. The method of claim 3, wherein the drop test is ASTM D5276-98 or ASTM D2463-10b (Procedure B).

17. The method of 16, wherein selecting the film structure comprises at least one of determining a number of layers within the film structure, determining a thickness of the film structure, determining the composition of each layer within the film structure, and determining manufacturing conditions for forming the film structure.

18. The method of claim 3, wherein the package is a pouch.

19. The method of claim 3, wherein the one or more desired tensile properties include elongation at break in the machine direction, elongation at break in the cross direction, stress at break in the machine direction, and stress at break in the cross direction.

20. The method of claim 3, wherein selecting a film structure further comprises minimizing the thickness of the film structure while providing the one or more desired tensile properties.

* * * * *